United States Patent [19]

Passi

[11] Patent Number: 5,524,627
[45] Date of Patent: Jun. 11, 1996

[54] ULTRASONIC IMAGING SYSTEM

[75] Inventor: Garri Passi, Rishon Le'Zion, Israel

[73] Assignee: Sonotron Ltd., Yavne, Israel

[21] Appl. No.: 294,713

[22] Filed: Aug. 23, 1994

[51] Int. Cl.$^6$ ............................................. A61B 8/00
[52] U.S. Cl. ........................................... 128/660.09
[58] Field of Search .................. 128/660.01, 660.02, 128/660.03, 660.04, 662.05, 662.06, 660.08, 660.09, 916

[56] References Cited

U.S. PATENT DOCUMENTS

| | | | |
|---|---|---|---|
| 5,203,337 | 4/1993 | Feldman | 128/662.06 |
| 5,398,690 | 3/1995 | Batten et al. | 128/662.06 |
| 5,425,370 | 6/1995 | Vilkomerson | 128/662.06 |

*Primary Examiner*—George Manuel
*Attorney, Agent, or Firm*—Mark M. Friedman

[57] ABSTRACT

An ultrasound imaging system for imaging an object. The system includes an ultrasonic probe for scanning the object, probe location monitoring apparatus for monitoring the actual trajectory of the ultrasonic probe with respect to the object, memory apparatus for storing scanning trajectories by which the object can be scanned by the ultrasonic probe and a display for displaying the actual trajectory of the ultrasonic probe superimposed on a background of one of the scanning trajectories. Furthermore, the system includes acoustic coupling monitoring apparatus for monitoring the degree of acoustic coupling between the ultrasonic probe and the object for each location of the ultrasonic probe, image correction apparatus for correcting images of the object by normalizing the images for each location of the probe according to an acoustic coupling reference value and an image display for displaying the image of the object.

15 Claims, 8 Drawing Sheets

ULTRASONIC IMAGING SYSTEM

FIELD AND BACKGROUND OF THE INVENTION

The present invention relates to ultrasonic imaging systems for imaging an object for the detection of flaws, defects, internal inhomogeneities and the like.

Ultrasonic imaging is used widely for detection of flaws, defects, internal inhomogeneities and the like in an object, for example, a welded joint. In principle, ultrasonic imaging involves imaging the object using an ultrasonic probe for transmitting a train of ultrasound energy pulses toward the object and for receiving the echo pulses reflected by the object. Display of the flaws, defects, internal inhomogeneities and the like in the object is achieved through the detection of changes in the amplitude and/or the travel time of the echo pulses. Several techniques of ultrasonic imaging are known in the art including A-scan imaging on an oscilloscope, B-scan imaging, C-scan imaging and P-scan imaging as described in an article entitled "Objectivization of the results of ultrasonic inspection of welding seams" by Dr. G. S. Passi in the English-language version of the Soviet Journal of Non-destructive testing, Vol. 23, No. 6, June, 1987, pgs. 372–379.

A conventional ultrasound imaging system, generally designated 10, will now be described with reference to FIG. 1. Ultrasound imaging system 10 includes an ultrasonic probe 12 for transmitting pulses of ultrasonic energy toward an object 14 under test, for example, a welded joint, and for receiving echo pulses reflected therefrom. Ultrasonic probe 12 is typically a hand-held implement for manipulation by an operator. The operator grips ultrasonic probe 12 and applies its head to object 14. The operator manipulates ultrasonic probe 12 over object 14 according to a trajectory stipulated by the type of object, size of object and other parameters. The operator typically holds ultrasonic probe 12 at normal incidence with respect to object 14. When the surface of object 14 is inaccessible or irregular, for example, in the case of the top bead of a weld, the operator is required to employ an angle ultrasonic probe.

The location of ultrasonic probe 12 on object 14 is determined by a probe location monitoring apparatus 16 providing real time feedback of the actual trajectory of ultrasonic probe 12 on object 14 to the operator. Probe location monitoring apparatus 16 typically includes an air acoustic emitter 18 for transmitting a signal and a receiver 20 for detecting the signal. Air acoustic emitter 18 is preferably integrated with ultrasonic probe 12 while receiver 20 is preferably in the form of two microphones 22 and 24 placed at a rightangle to one another for providing a Cartesian co-ordinate system. The degree of acoustic coupling between ultrasonic probe 12 and object 14 is determined by an acoustic coupling monitoring apparatus 26. Acoustic coupling monitoring apparatus 26 typically includes a low frequency noise vibrator 28 for transmitting a reference signal into object 14 for pick up by ultrasonic probe 12.

System 10 further includes digital computer apparatus 30 for generating a scan image of object 14 by correlating between the amplitude and/or time delays of echo pulses received by ultrasonic probe 12 and the location of ultrasonic probe 12 as provided by probe location monitoring apparatus 16. Hence, digital computer apparatus 30 includes a defect image array 32 for storing data regarding the flaws, defects and internal inhomogeneities, if any, detected in object 14 and a trajectory image array 34 for storing data regarding the actual trajectory of ultrasonic probe 12 with respect to object 14. Defects image array 32 displays the images of object 14 on an image display 36 which typically displays a "Top View" image 38 of object 14, a "Side View" image 40 of object 14 and an "End View" image 42 of object 14. For the sake of exposition, different views of a defect 44 in object 14 are shown in Top View image 38, Side View image 40 and End View image 42.

Digital computer apparatus 30 also displays the actual trajectory of ultrasonic probe 12 on the surface of object 14 on a trajectory display 46. The actual trajectory, generally designated 48, includes zones 50 where the acoustic coupling between ultrasonic probe 12 and object 14 is equal to or greater than a pre-determined threshold and zones 52 which suffer from an insufficient degree of acoustic coupling between ultrasonic probe 12 and object 14. For the sake of clarity, the equivalent of trajectory 48 has been represented by a partly broken trajectory on object 14.

It is well known that the images of flaws, defects, internal inhomogeneities and the like rendered by ultrasound imaging suffer from a number of deficiencies due to the manual manipulation of the probe. These deficiencies include the proficiency that an operator performs the scanning trajectory, the consistency of the acoustic coupling between the ultrasonic probe and the object under test as determined by the pressure applied by the operator, the angle that the operator holds the probe with respect to the object, and the like. Other deficiencies include that trajectory display 46 does not provide indication of which areas of the object have been scanned by ultrasonic probe 12 or the location of ultrasonic probe 12 with respect to object 14 when there is no acoustic coupling therebetween.

Turning now to FIG. 2, ultrasound imaging system 10 includes an angle ultrasonic probe 54 for imaging an object 14 when some or all of the portion of object 14 to be scanned is inaccessible. Angle ultrasonic probe 54 includes a scanning ultrasonic crystal 56 connected to digital computing apparatus 30 and an acoustic coupling ultrasonic crystal 58 connected to acoustic coupling monitoring apparatus designated 60 to distinguish it from acoustic coupling monitoring apparatus 26. In addition, system 10 employs a synchronizer 62 to ensure that there is no interference between the operation of scanning ultrasonic crystal 56 and acoustic coupling ultrasonic crystal 58. As can be clearly seen, scanning ultrasonic crystal 56 is inclined at an angle to object 14 while acoustic coupling ultrasonic crystal 58 is substantially normal to object 14. In this case, acoustic coupling monitoring apparatus 60 compares the level of the first backwall echo pulse from the backwall of object 14 to a threshold to determine zones 50 where the acoustic coupling between scanning ultrasonic probe 56 and object 14 is equal to or greater than the pre-determined threshold and zones 52 which suffer from an insufficient degree of acoustic coupling between scanning ultrasonic probe 56 and object 14. It is well known that acoustic coupling monitoring apparatus 60 suffers from low reliability due to the amplitude of backwall echo pulses depending not only on the state of the acoustic coupling but on other factors, for example, the local changing curvature of the tested objects, local non-parallelity of tested objects' surfaces, structural inhomogeneities in the tested objects, and the like. Furthermore, ultrasound imaging using an angle ultrasonic probe suffers from similar deficiencies as conventional probes due to the manual manipulation of the probe.

There is therefore a need for ultrasound imaging systems for imaging objects for the detection of flaws, defects, inherent inhomogeneities and the like in objects overcoming the deficiencies of conventional ultrasound imaging systems.

SUMMARY OF THE INVENTION

The present invention is for ultrasound imaging systems for imaging objects for the detection of flaws, defects, inherent inhomogeneities and the like.

Hence, there is provided according to the teachings of the present invention, an ultrasound imaging system for imaging an object, the system comprising: (a) an ultrasonic probe for scanning the object; (b) probe location monitoring apparatus for monitoring the actual trajectory of the ultrasonic probe with respect to the object; (c) a memory for storing at least one scanning trajectory by which the object can be scanned by the ultrasonic probe; and (d) a trajectory display for displaying the actual trajectory of the ultrasonic probe superimposed on a background of one of the at least one scanning trajectory.

According to a further feature of the present invention, the trajectory display provides a perceptible signal corresponding to the current location of the ultrasonic probe with respect to the object.

According to a still further feature of the present invention, the trajectory display displays at least the scanned portion of the object.

According to a yet still further feature of the present invention, the system further comprising selection apparatus for selecting one of the at least one scanning trajectory.

According to a yet still further feature of the present invention, the system further comprising: (e) acoustic coupling monitoring apparatus for monitoring the degree of acoustic coupling between the ultrasonic probe and the object for each location of the ultrasonic probe on the object; (f) image correction apparatus for correcting at least one image of the object by normalizing the at least one image for each location of the probe according to an acoustic coupling reference value; and (g) an image display for displaying the at least one image of the object.

There is also provided according to the teachings of the present invention, an ultrasound imaging system for imaging an object, the system comprising: (a) an ultrasonic probe for scanning the object; (b) probe location monitoring apparatus for monitoring the location of the ultrasonic probe with respect to the object; (c) acoustic coupling monitoring apparatus for monitoring the degree of acoustic coupling between the ultrasonic probe and the object for each location of the probe; (d) image correction apparatus for correcting at least one image of the object by normalizing the at least one image for each location of the ultrasonic probe according to an acoustic coupling reference value; and (e) an image display for displaying the at least one image of the object.

According to a further feature of the present invention, the system further comprising: (f) probe location monitoring apparatus for monitoring the actual trajectory of the ultrasonic probe with respect to the object; (g) a memory for storing at least one scanning trajectory by which the object can be scanned by the ultrasonic probe; and (h) a trajectory display for displaying the actual trajectory of the ultrasonic probe superimposed on a background of one of the at least one scanning trajectory.

According to a still further feature of the present invention, the trajectory display provides a perceptible signal corresponding to the current location of the ultrasonic probe with respect to the object.

According to a yet still further feature of the present invention, the trajectory display displays at least the scanned portion of the object.

According to a yet still further feature of the present invention, the system further comprising selection apparatus for selecting one of the at least one scanning trajectory.

There is further provided according to the teachings of the present invention, an ultrasound imaging system for imaging an object, the ultrasound imaging system including an acoustic coupling monitoring apparatus comprising: (a) an ultrasonic probe for providing reference pulses for reflection by a backwall of the object; (b) a first peak detector for detecting a first signal associated with a first backwall echo from the backwall; (c) a first comparator for comparing the first signal to a first threshold; (d) a second peak detector for detecting a second signal associated with a second backwall echo from the backwall; and (e) a second comparator for comparing the ratio between the first signal and the second signal to a second threshold.

According to a still further feature of the present invention, the system further comprising: (f) an ultrasonic probe for scanning the object; (g) probe location monitoring apparatus for monitoring the actual trajectory of the ultrasonic probe with respect to the object; (h) a memory for storing at least one scanning trajectory by which the object can be scanned by the ultrasonic probe; and (i) a trajectory display for displaying the actual trajectory of the ultrasonic probe superimposed on a background of one of the at least one scanning trajectory.

According to a further feature of the present invention, the trajectory display provides a perceptible signal corresponding to the current location of the ultrasonic probe with respect to the object.

According to a still further feature of the present invention, the trajectory display displays at least the scanned portion of the object.

According to a yet still further feature of the present invention, the system further comprising selection apparatus for selecting one of the at least one scanning trajectory.

According to a yet still further feature of the present invention, the system further comprising: (j) image correction apparatus for correcting at least one image of the object by normalizing the at least one image for each location of the probe according to an acoustic coupling reference value; and (k) an image display for displaying the at least one image of the object.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of ultrasound imaging systems for imaging objects for the detection of flaws, defects, internal inhomogeneities and the like.

The principles and operation of ultrasound imaging systems for detecting flaws, defects, internal inhomogeneities and the like according to the present invention may be better understood with reference to the drawings and the accompanying description.

Figure 3:
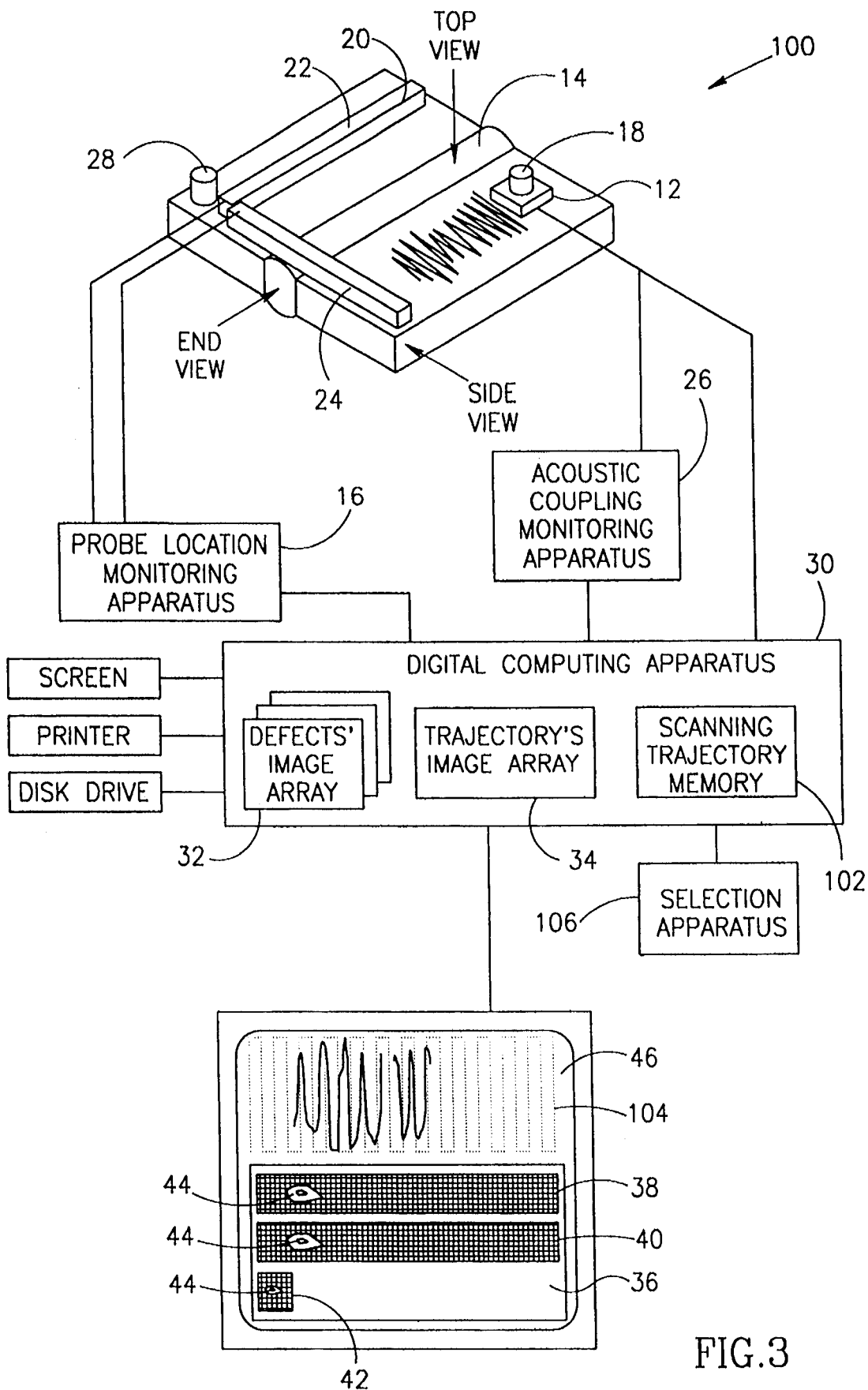
FIG. 3 is a schematic illustration of a first embodiment of an ultrasound imaging system for imaging an object according to the teachings of the present invention.

Referring now to the drawings, FIG. 3 illustrates a preferred embodiment of an ultrasound imaging system, generally designated 100, constructed and operative according to the teachings of the present invention, for imaging objects for the detection of flaws, defects, internal inhomogeneities, and the like. Ultrasound imaging system 100 is similar to ultrasound imaging system 10 and therefore common elements are denoted with similar reference numbers used to describe ultrasound imaging system 10.

Hence, ultrasound imaging system 100 includes ultrasonic probe 12 for imaging an object 14, probe location monitoring apparatus 16 for providing the location of ultrasonic probe 12 on object 14 and acoustic coupling monitoring apparatus 26 for providing the degree of acoustic coupling between ultrasonic probe 12 and object 14. Furthermore, system 100 includes digital computer apparatus 30 including defect image array 32 for displaying the images of object 14 on image display 36 and trajectory image array 34 for displaying the actual trajectory of ultrasonic probe 12 on the surface of object 14 on trajectory display 46.

It is a particular feature of system 100 that digital computer apparatus 30 further includes a scanning trajectory memory 102 for storing at least one scanning trajectory by which object 14 can be scanned by ultrasonic probe 12. As shown, actual trajectory 48 is preferably superimposed on scanning trajectory 104 retrieved from memory 102 on trajectory display 46 during the scanning of object 14 to provide real time feedback to the operator on two parameters. First, the proficiency by which the operator follows scanning trajectory 104. And second, the consistency of the acoustic coupling between ultrasonic probe 12 and object 14 in terms of the pressure the operator is applying and the angle that he is maintaining between ultrasonic probe 12 and object 14. In the case that scanning trajectory library 102 includes more than one scanning trajectory 104, system 100 includes selection apparatus 106 for selecting one of the scanning trajectories for display on trajectory display 46.

Figure 4:
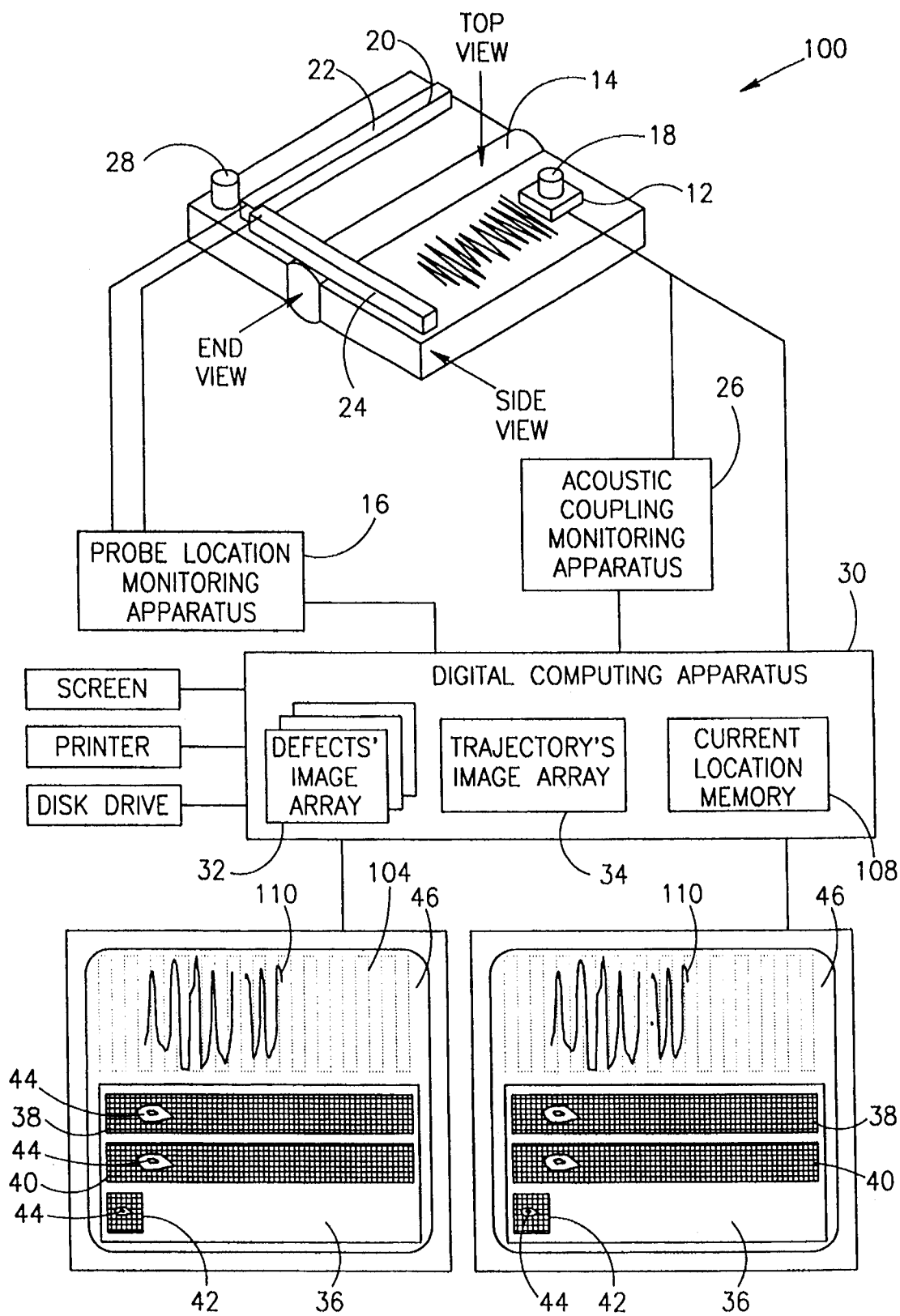
FIG. 4 is a schematic illustration of a second embodiment of an ultrasound imaging system for imaging an object according to the teachings of the present invention.

With reference now to FIG. 4, it is a further feature of system 100 that digital computer apparatus 30 includes a current location memory 108 for providing a blinking cursor 110 corresponding to the location of ultrasonic probe 12 on object 14. It should be noted that memory 108 receives input from probe location monitoring apparatus 26 only such that blinking cursor 110 is provided irrespective of whether acoustic coupling between ultrasonic probe 12 and object 14 is established. Furthermore, it should be noted that memory 108 is operative without memory 102 providing a scanning trajectory on trajectory display 46.

Figure 5:
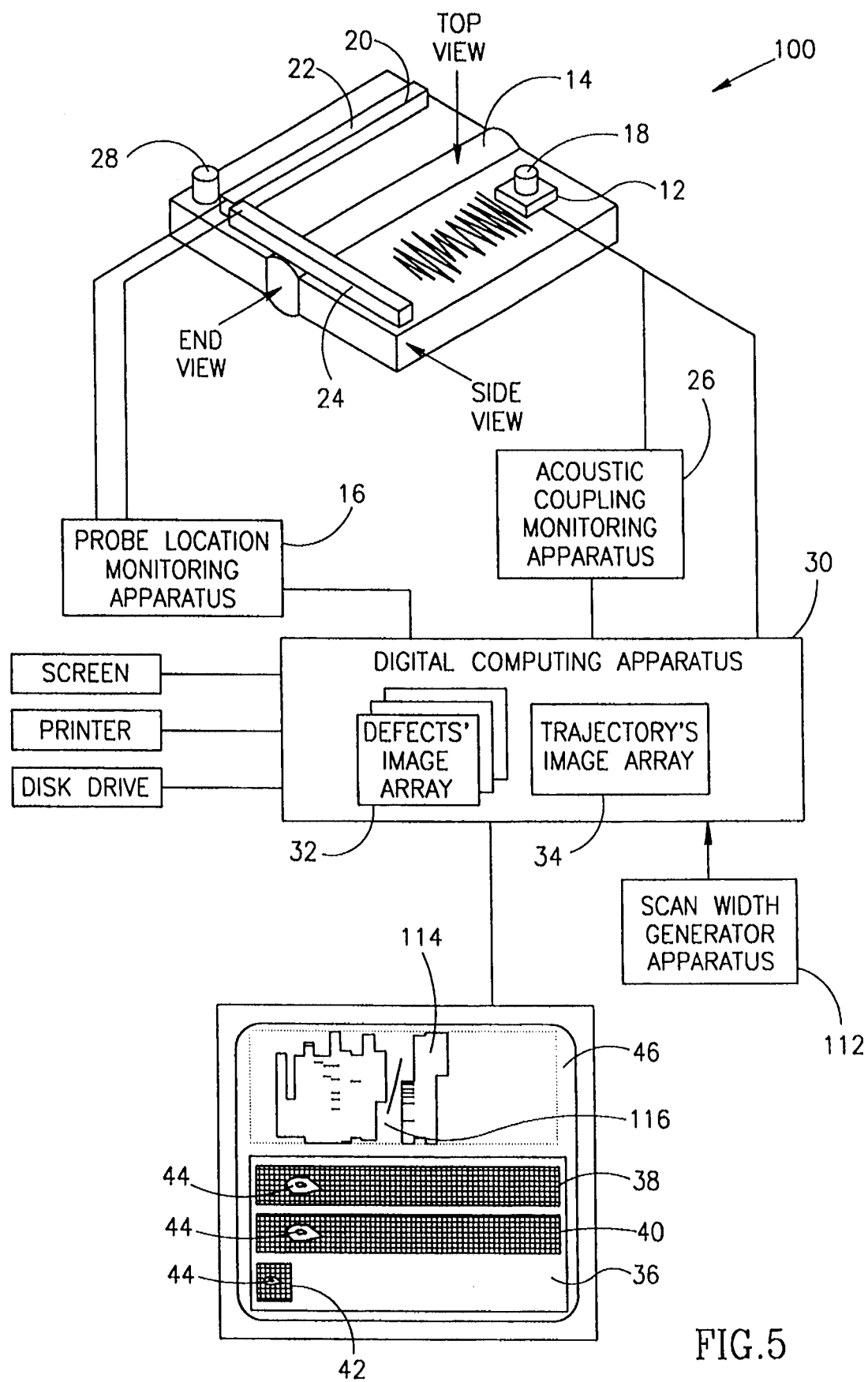
FIG. 5 is a schematic illustration of a third embodiment of an ultrasound imaging system for imaging an object according to the teachings of the present invention.

With reference now to FIG. 5, it is a still further feature of present invention that system 100 includes a scan width generator apparatus 112 for providing the scan width of ultrasonic probe 14. Generally speaking, scan width generator apparatus 112 generates the scan width of ultrasonic probe 12 by taking into consideration the width of the head of ultrasonic probe 12, the desired gain of system 100, and the degree of acoustic coupling between ultrasonic probe 12 and object 14. In the case, that system 100 includes memory 102, the scanning trajectories are adjusted to accommodate the scan width of ultrasonic probe 12 such that the scanning trajectories require the minimum number of passes of ultrasonic probe 12 on object 14.

Figure 1:
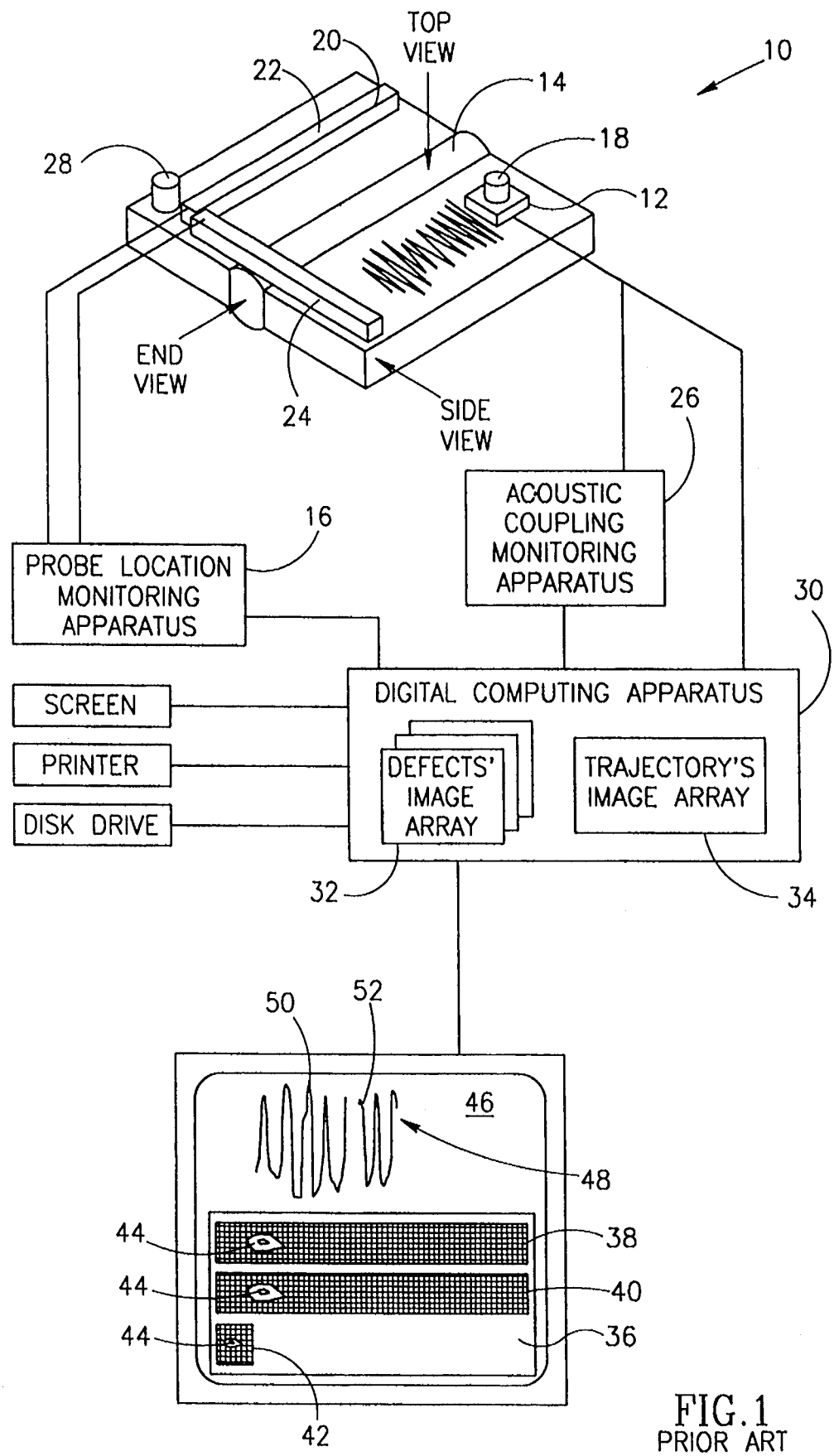
FIG. 1 is a schematic illustration of a conventional ultrasound imaging system.
Figure 2:
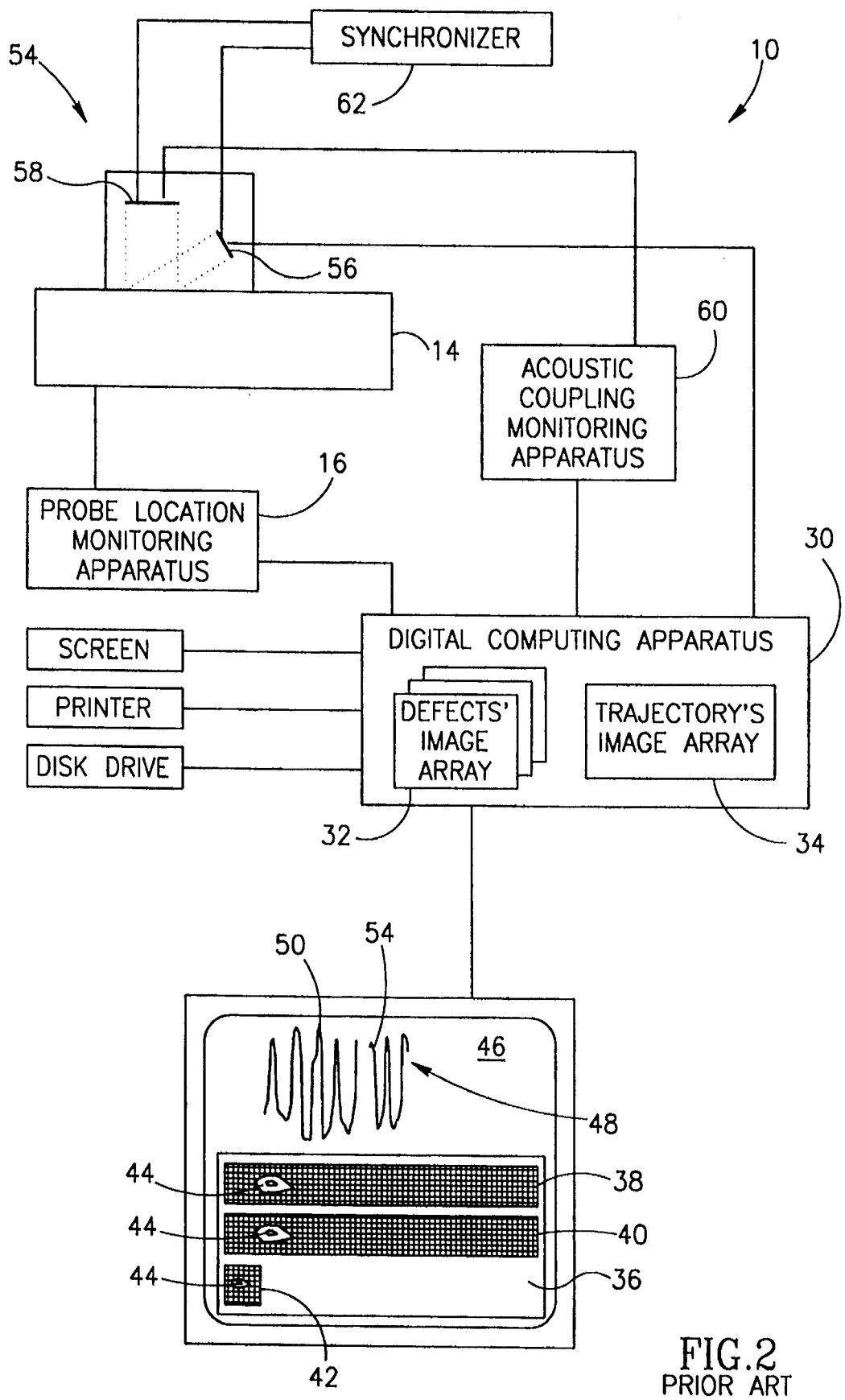
FIG. 2 is a schematic illustration of a conventional ultrasound imaging system including an angle ultrasonic probe with a scanning ultrasonic crystal and an acoustic coupling ultrasonic crystal.

As shown, the scanned portion of object 14 is shown on trajectory display 46 during the scanning of object 14 in a similar fashion to actual trajectory 48 to provide real time feedback to the operator on the proficiency by which the operator is executing the scanning operation. In this case, zones 50, additionally designated 114, and zones 52, additionally designated 116, can be far better appreciated by the operator than zones 50 and 52 depicted on trajectory display 46 of FIG. 1.

Figure 6A:
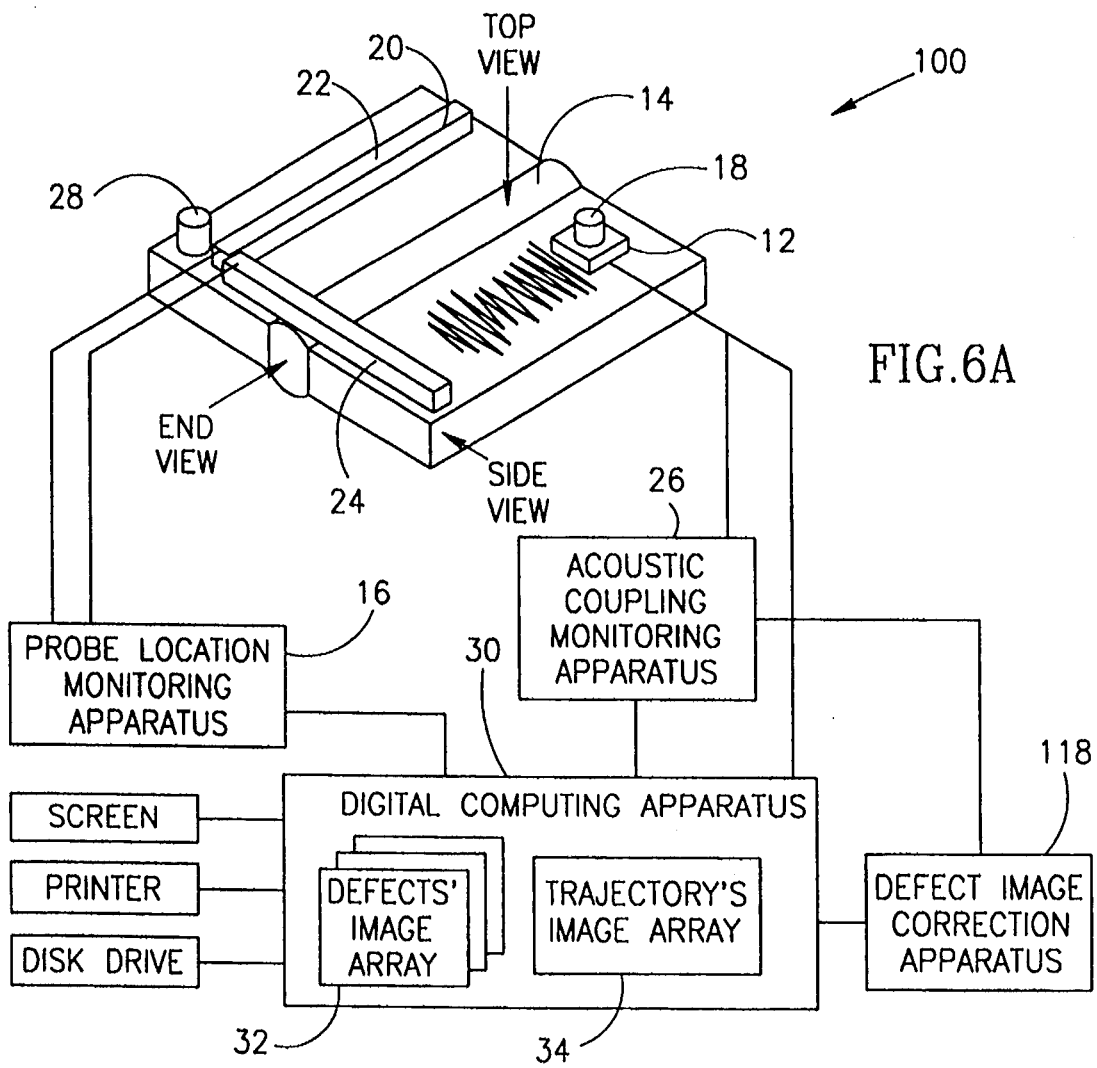
FIG. 6 is a schematic illustration of a fourth embodiment of an ultrasound imaging system for imaging an object according to the teachings of the present invention.
Figure 6B:
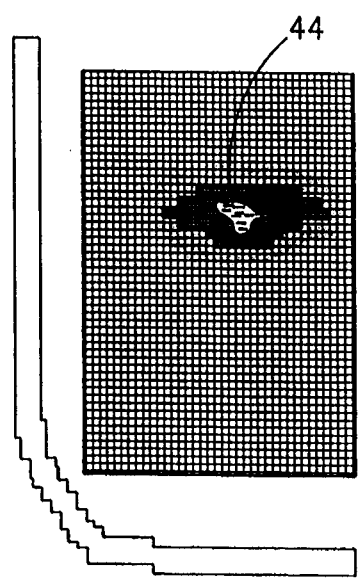
Figure 6C:
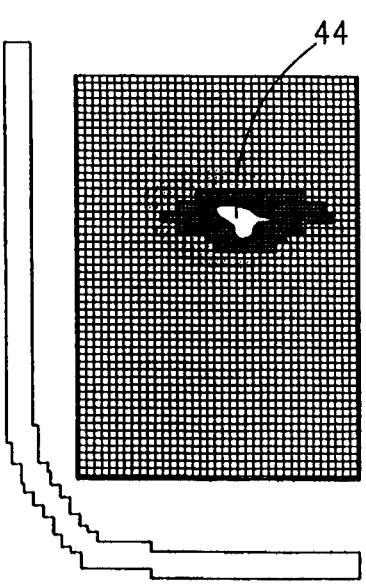

With reference now to FIG. 6, it is a yet still further feature of the present invention that system 100 includes defect image correction apparatus 118 for correcting Top View image 38, Side View image 40 and End View image 42. This is achieved by defect image correction apparatus 118 normalizing data stored in defects image array 32 for each location of ultrasonic probe 12 according to an acoustic coupling reference value. Typically, the acoustic coupling reference value is the highest reading measured by acoustic coupling monitoring apparatus 26. As can be clearly be seen on comparing the two defect images of FIG. 6, the corrected defect image on the right is far more discernible than the uncorrected defect image on the left.

Figure 7A:
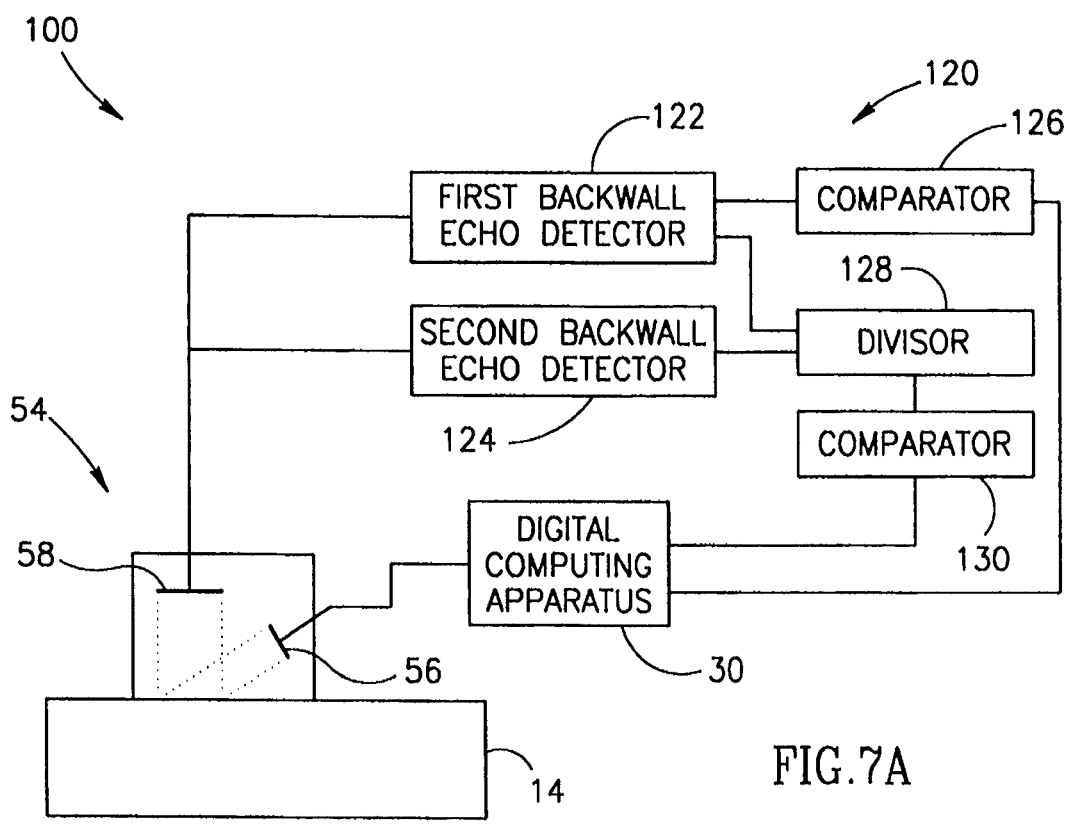
FIG. 7a is a schematic illustration of a fifth embodiment of an ultrasound imaging system including an improved acoustic coupling monitoring system for angle ultrasonic probes according to the teachings of the present invention.
Figure 7B:
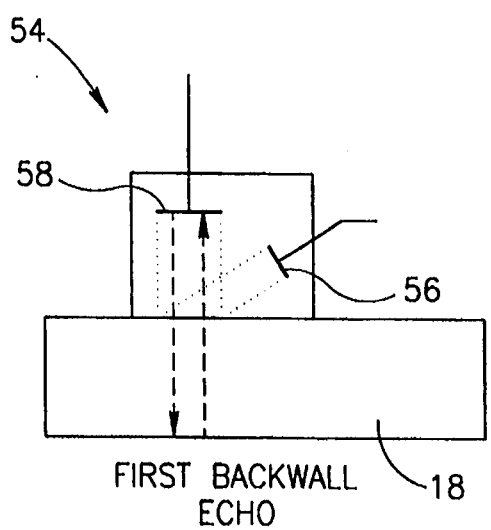
FIG. 7b is a schematic illustration of the passage of a reference pulse from an acoustic coupling ultrasonic probe through an object.

With reference now to FIG. 7a, the schematic illustration depicts an acoustic coupling monitoring apparatus 120 adapted for improving the sensitivity of the monitoring of acoustic coupling between angle ultrasonic probe 54 and object 14. Generally speaking, acoustic coupling monitoring apparatus 120 includes a first peak detector 122 and a second peak detector 124 for detecting the amplitude of the first and second backwall echoes of a reference signal, respectively, provided by acoustic coupling ultrasonic crystal 58. Turning briefly to FIG. 7b, it can be appreciated that the amplitude of the first backwall echo is greater than the amplitude of the second backwall echo because the first backwall echo passes through object 14 twice between its transmission and receiving by ultrasonic crystal 58 while the second backwall echo passes through object 14 four times between its transmission and receiving by ultrasonic crystal 58.

Acoustic coupling monitoring apparatus 120 also includes a first comparator 126 for comparing the amplitude of the first signal to a first threshold, a divisor 128 for providing a ratio obtained by dividing the amplitude of the first backwall echo as detected by peak detector 122 by the amplitude of the second backwall echo as detected by peak detector 124, and a second comparator 130 for comparing the ratio from divisor 128 to a second threshold. Hence, all in all, acoustic coupling monitoring apparatus 120 applies two consecutive comparisons for determining whether the degree of acoustic coupling between angle ultrasonic probe 54 and object 14 should be indicated on trajectory display 46 as zone 50 or zone 52 as follows. First, comparator 126 compares the amplitude of the first signal to a first threshold. If the amplitude is equal to or greater than the threshold, then the acoustic coupling at that particular location is registered on trajectory display 46 as zone 50. If the amplitude is less than the threshold, then comparator 130 compares the ratio to a second threshold. If the ratio is equal to or greater than the second threshold, then the acoustic coupling at that particular location is registered on trajectory display 46 as zone 50. However, if the ratio is less than the second threshold, then the acoustic coupling at that particular location is registered on trajectory display 46 as zone 52.

Figure 7B:
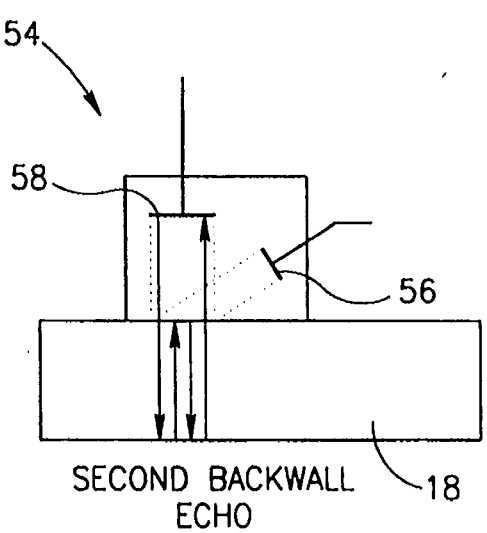
Figure 8:
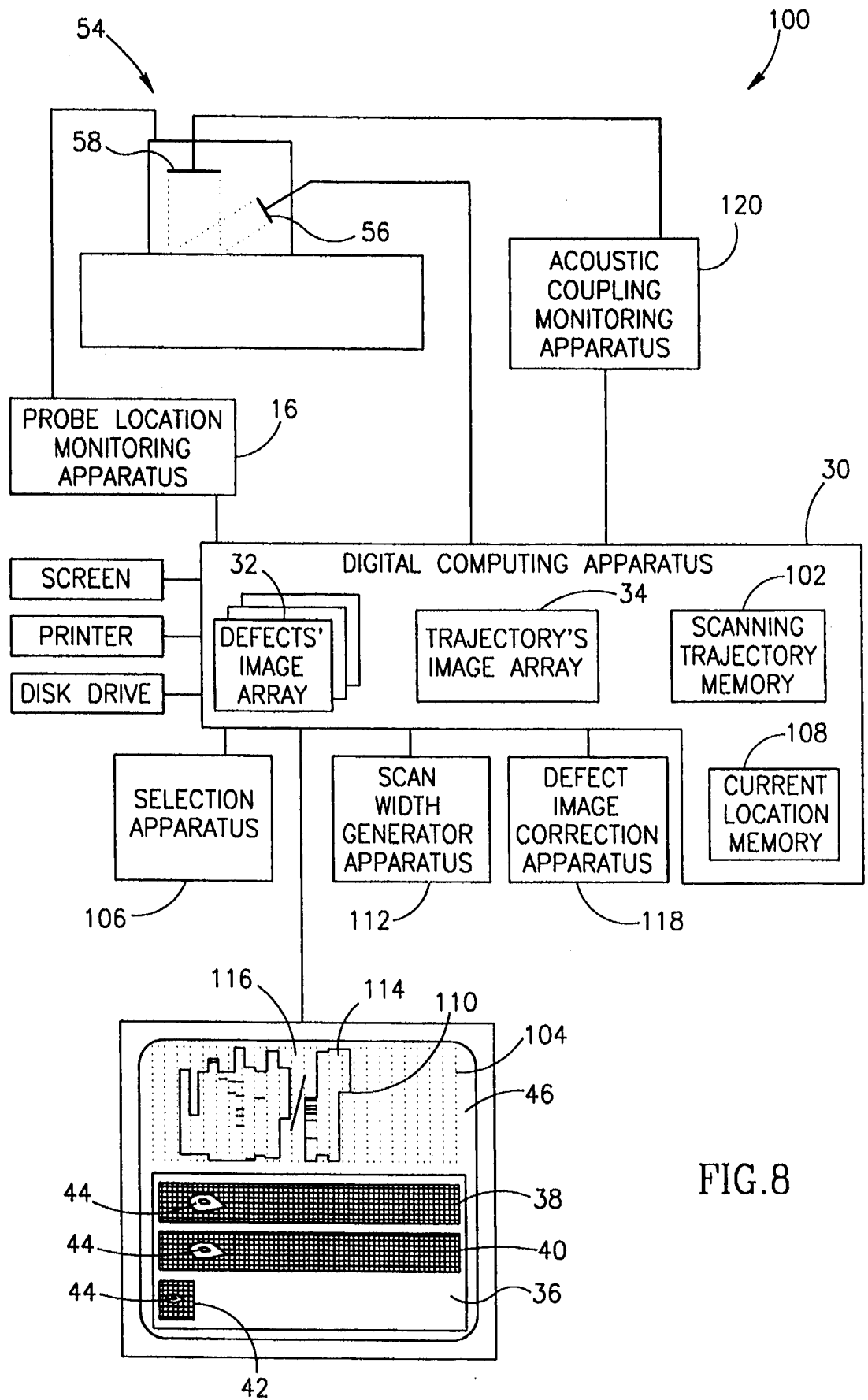
FIG. 8 is a schematic illustration of the ultrasound imaging system of FIG. 7 including other improvements according to the teachings of the present invention.

With reference now to FIG. 8, the schematic illustration depicts an ultrasound imaging system 100 including scanning trajectory memory 102 and selection apparatus 106 for providing scanning trajectory 104 on trajectory display 46 as described in FIG. 3, current location memory 108 for providing blinking cursor 110 on trajectory display 46 as described in FIG. 4, scan width generation apparatus 112 for providing the scanned portion of the object on trajectory display 46 as described in FIG. 5, defect image correction apparatus 118 for correcting images of defects on image display 36 as described in FIG. 6 and acoustic coupling monitoring apparatus 120 as described in FIG. 7.

While the invention has been described with respect to a limited number of embodiments, it will be appreciated that many variations, modifications and other applications of the invention may be made.

What is claimed is:

1. An ultrasound imaging system for imaging an object, the system comprising:
   (a) an ultrasonic probe for scanning the object;
   (b) probe location monitoring apparatus for monitoring the actual trajectory of said ultrasonic probe with respect to the object;
   (c) a memory for storing at least one scanning trajectory by which the object can be scanned by said ultrasonic probe;
   (d) a trajectory display for displaying the actual trajectory of said ultrasonic probe superimposed on a background of one of said at least one scanning trajectory;
   (e) acoustic coupling monitoring apparatus for monitoring the degree of acoustic coupling between said ultrasonic probe and the object for each location of said ultrasonic probe on the object;
   (f) image correction apparatus for correcting at least one image of the object by normalizing said at least one image for each location of said probe according to an acoustic coupling reference value; and
   (g) an image display for displaying said at least one image of the object.

2. The system as in claim 1, wherein said trajectory display provides a perceptible signal corresponding to the current location of said ultrasonic probe with respect to the object.

3. The system as in claim 1, wherein said trajectory display displays at least the scanned portion of the object.

4. The system as in claim 1, further comprising selection apparatus for selecting one of said at least one scanning trajectory.

5. An ultrasound imaging system for imaging an object, the system comprising:
   (a) an ultrasonic probe for scanning the object;
   (b) probe location monitoring apparatus for monitoring the location of said ultrasonic probe with respect to the object;
   (c) acoustic coupling monitoring apparatus for monitoring the degree of acoustic coupling between said ultrasonic probe and the object for each location of said probe;
   (d) image correction apparatus for correcting at least one image of the object by normalizing said at least one image for each location of said ultrasonic probe according to an acoustic coupling reference value; and
   (e) an image display for displaying said at least one image of the object.

6. The system as in claim 5, further comprising:
   (f) probe location monitoring apparatus for monitoring the actual trajectory of said ultrasonic probe with respect to the object;
   (g) a memory for storing at least one scanning trajectory by which the object can be scanned by said ultrasonic probe; and
   (h) a trajectory display for displaying the actual trajectory of said ultrasonic probe superimposed on a background of one of said at least one scanning trajectory.

7. The system as in claim 6, wherein said trajectory display provides a perceptible signal corresponding to the current location of said ultrasonic probe with respect to the object.

8. The system as in claim 6, wherein said trajectory display displays at least the scanned portion of the object.

9. The system as in claim 6, further comprising selection apparatus for selecting one of said at least one scanning trajectory.

10. An ultrasound imaging system for imaging an object, the ultrasound imaging system including an acoustic coupling monitoring apparatus comprising:
    (a) an ultrasonic probe for providing reference pulses for reflection by a backwall of the object;
    (b) a first peak detector for detecting a first signal associated with a first backwall echo from the said backwall;
    (c) a first comparator for comparing said first signal to a first threshold;
    (d) a second peak detector for detecting a second signal associated with a second backwall echo from said backwall; and
    (e) a second comparator for comparing the ratio between said first signal to said second signal to a second threshold.

11. The system as in claim 10, further comprising:
    (f) an ultrasonic probe for scanning the object;
    (g) probe location monitoring apparatus for monitoring the actual trajectory of said ultrasonic probe with respect to the object;
    (h) a memory for storing at least one scanning trajectory by which the object can be scanned by said ultrasonic probe; and
    (i) a trajectory display for displaying the actual trajectory of said ultrasonic probe superimposed on a background of one of said at least one scanning trajectory.

12. The system as in claim 11, wherein said trajectory display provides a perceptible signal corresponding to the current location of said ultrasonic probe with respect to the object.

13. The system as in claim 11, wherein said trajectory display displays at least the scanned portion of the object.

14. The system as in claim 11, further comprising selection apparatus for selecting one of said at least one scanning trajectory.

15. The system as in claim 10, further comprising:

(j) image correction apparatus for correcting at least one image of the object by normalizing said at least one image for each location of said probe according to an acoustic coupling reference value; and (k) an image display for displaying said at least one image of the object.

* * * * *